United States Patent [19]

Sculco et al.

[11] Patent Number: 4,731,087

[45] Date of Patent: Mar. 15, 1988

[54] METATARSAL-PHALANGEAL PROSTHESIS

[75] Inventors: Thomas P. Sculco, New York, N.Y.; Albert H. Burstein; Timothy M. Wright, both of Stamford, Conn.

[73] Assignee: New York Society for the Relief of the Ruptured and Crippled, New York, N.Y.

[21] Appl. No.: 662

[22] Filed: Jan. 6, 1987

[51] Int. Cl.$^4$ .............................................. A61F 2/42
[52] U.S. Cl. .................................................... 623/21
[58] Field of Search ...................... 623/21, 20, 18, 16

[56] References Cited

U.S. PATENT DOCUMENTS

| | | | |
|---|---|---|---|
| 3,992,726 | 11/1976 | Freeman et al. | 623/18 |
| 4,156,296 | 5/1979 | Johnson et al. | 623/21 |
| 4,205,400 | 6/1980 | Shen et al. | 623/20 X |
| 4,257,129 | 3/1981 | Volz | 623/20 |
| 4,568,348 | 2/1986 | Johnson et al. | 623/20 |

OTHER PUBLICATIONS

Catalog page of Richards Manufacturing Co., Inc., Great Toe Total First, p. 63, 1981, 623-21.

*Primary Examiner*—Ronald L. Frinks
*Attorney, Agent, or Firm*—Brumbaugh, Graves, Donohue & Raymond

[57] ABSTRACT

A prosthesis for replacement of the first metatarsal-phalangeal articulation comprises a metatarsal component and a phalangeal component. The metatarsal component has a convex articulating surface and concave distal aspect, the metatarsal articulating surface being curved so as to approximate the natural articular surface of the first metatarsal bone and furthermore to articulate smoothly with the phalangeal articulating surface of the phalangeal component. The phalangeal component comprises a base member and an insert, the base member having a distal aspect adapted to engage and be secured to a resected end of the phalanx bone and also having a proximal aspect adapted to receive and have permanently attached thereto the insert. The insert, which includes the phalangeal articulating surface, is made available in various distal-proximal thicknesses, and an appropriately sized insert is selected during implantation so as to cause the tension in the natural soft tissue surrounding the prosthesis after implantation to approximate the tension of the soft tissue of the natural metatarsal-phalangeal articulation.

8 Claims, 12 Drawing Figures

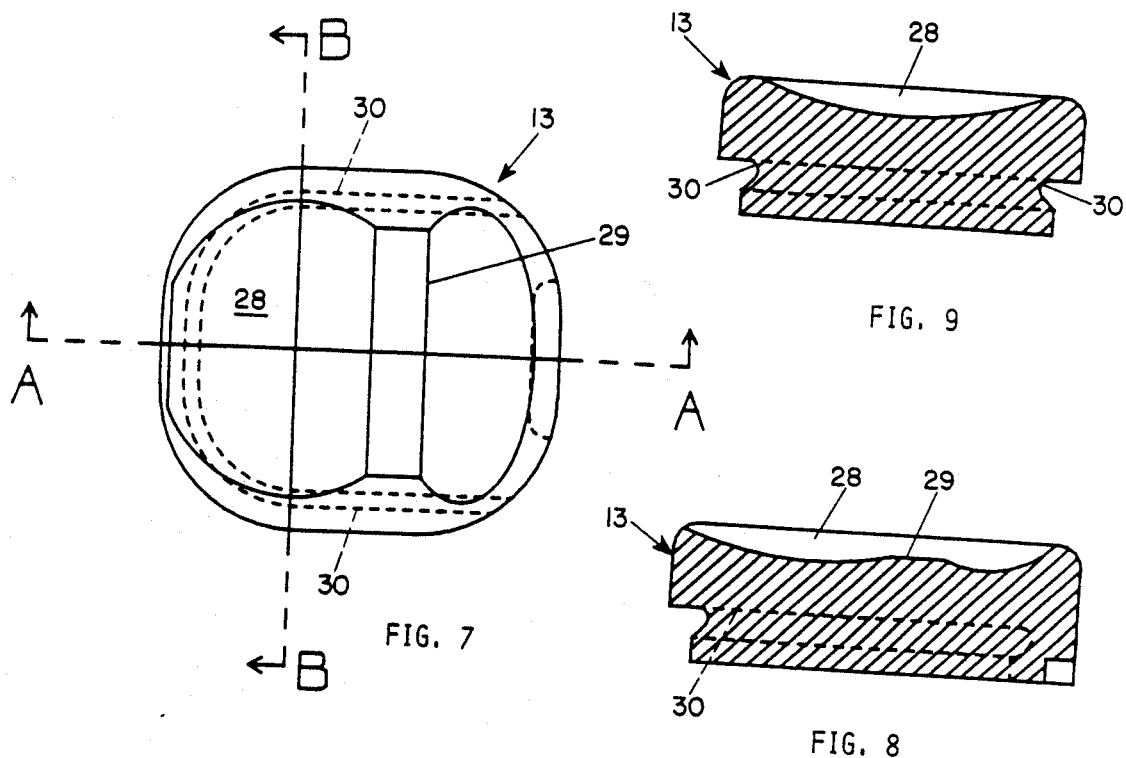
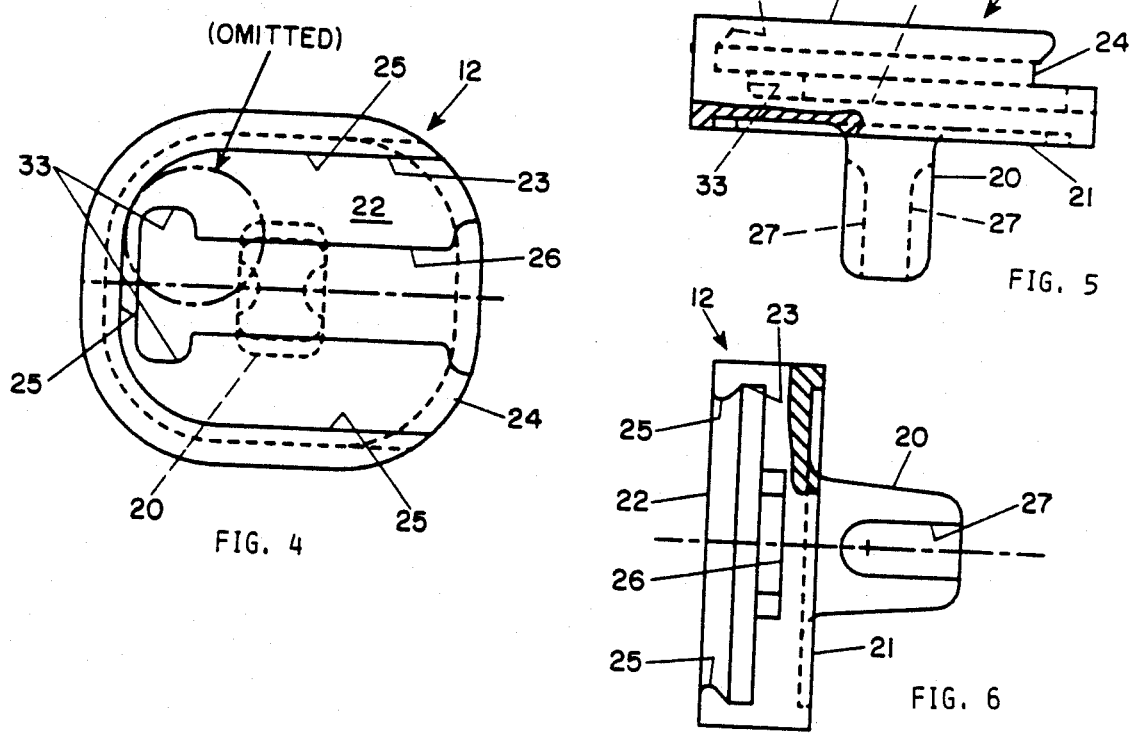

METATARSAL-PHALANGEAL PROSTHESIS

DESCRIPTION

Background of the Invention

The present invention relates to a bicondylar toe joint prosthesis intended for the replacement of degenerated first metatarsal-phalangeal articulations and to a method for implanting the prosthesis. Degeneration of the first metatarsal-phalangeal articulation occurs most commonly in patients with osteoarthritis, hallux rigidus or rheumatoid arthritis, and in severe cases can impede or even prevent walking movement. As anyone with a sprained or broken great toe will attest, the first metatarsal-phalangeal articulation undergoes substantial stress even during normal walking and any degeneration or injury can cause debilitating pain.

Toe joint prostheses are known in the art. For example, there is what is known as the Great Toe Total First prosthesis marketed by Richards Medical Company. This prosthesis comprises two components, a metatarsal component and a phalangeal component. The metatarsal component is of cobalt chrome alloy and has a convex articulating surface which corresponds to and replaces the convex condyle of the first metatarsal bone. The phalangeal component is constructed of ultra high molecular weight polyethylene (UHMWPE) and has a concave surface for articulation with the convex surface of the metatarsal component.

Both the metatarsal and phalangeal components have stem portions and are cemented, respectively, to the metatarsal and the proximal phalanx bones. Both of these bones are surgically resected to receive the prosthesis components, e.g. by forming a precisely sized and shaped recess for the stem portion.

An eminence (ridge) is provided on the phalangeal component while a corresponding mating groove is provided on the metatarsal component. When mated and under compression this feature provides a limited amount of medial-lateral (M-L) restraint. As with all joints, compression is always present in the metatarsal-phalangeal joint and loads can be quite high during certain parts of the walking cycle. Because of the inherent geometric articulating constraint, the higher the compressive loads, the higher the resistance this design must provide to M-L shear at the joint surface.

Most of the resistance to shear and rotation comes from the natural or surgically reconstructed soft tissue surrounding the prosthesis. It is therefore important that the proper amount of tension be provided in the supporting ligaments and/or tendons by the surgeon. Given the relatively small size of the metatarsal-phalangeal joint, particularly as compared to the high loads the joint must bear, the margin for error in establishing the proper tension is quite small and the tensioning procedure can be a delicate and difficult one.

Normal anatomic plantar flexion-dorsi flexion motion (F-E-M) is 135° total, which consists of 45° passive flexion and 90° passive extension. The articular surface of this prior art prosthesis typically allows a maximum of 60° passive flexion and 0° passive extension. Additionally, the prosthesis must rely on a nondiseased dorsal portion of the metatarsal bone to articulate with its phalangeal component when in extension. Unfortunately, this surface is not always in good functional condition in patients with osteoarthritis, hallux rigidus or rheumatoid arthritis, the conditions most often calling for total metatarsal-phalangeal joint resurfacing procedures.

Also, there is described in U.S. Pat. No. 4,156,296 a prosthesis which comprises only two components, a metatarsal component and a phalangeal component. The two components articulate on part-spherical convex and concave surfaces, respectively, and these surfaces are therefore free to slide relative to each other in a universal manner. Such an articulation does not approximate the natural metatarsal-phalangeal articulation which has a mating groove-ridge configuration.

SUMMARY OF THE INVENTION

The present invention is a metatarsal-phalangeal prosthesis which offers significant advantages over devices heretofore employed. Instead of comprising only two components, which must be selected for size in advance and then properly tensioned by the surgeon, the present invention includes four separate components, three of which are combined to make the phalangeal component.

Thus the phalangeal component comprises a base member, a plastic insert and a retaining clip for permanently attaching the insert to the base member. In actual practice, the plastic insert (which includes the concave surface which articulates with the metatarsal component) serves as a spacer which greatly facilitates the tensioning of the ligaments and/or tendons. Variously sized inserts may be made available, and the insert that achieves the desired tension can then be selected. In selecting the appropriate insert, the surgeon may use temporary spacer blocks (e.g. 10 mm, 12 mm, 14 mm, 16 mm and 18 mm thickness) labeled so as to indicate the insert that corresponds to the spacer block found to provide the proper tension.

In the preferred embodiments, the prosthesis is provided in left and right foot versions. In the natural metatarsal-phalangeal joint, the ridge-groove pattern on the respective articulating surfaces is not centrally located but is instead offset toward the medial side of the foot. Therefore the preferred embodiments approximate this offset so as to provide movement and withstand loads in as natural a manner as possible.

DESCRIPTION OF THE DRAWINGS

FIG. 4 is an elevational view of the proximal aspect of the base member of the phalangeal component for either a right or left foot prosthesis, but oriented about its proximal-distal axis so as to receive a plastic insert which will articulate with the right foot metatarsal component depicted in FIGS. 1 to 3;

FIG. 5 is a plan view of the lateral aspect of the base member depicted in FIG. 4.

FIG. 6 is a side elevational view of the lateral aspect of the base member depicted in FIG. 4.

FIG. 7 is an elevational view of the plastic insert for either a right or left foot prosthesis, but oriented about its proximal-distal axis so as to articulate with the right foot metatarsal component depicted in FIGS. 1 to 3.

FIG. 8 is a sectional view taken along plane A-A of FIG. 7.

FIG. 9 is a sectional view taken along plane B-B of FIG. 7.

Figure 10:
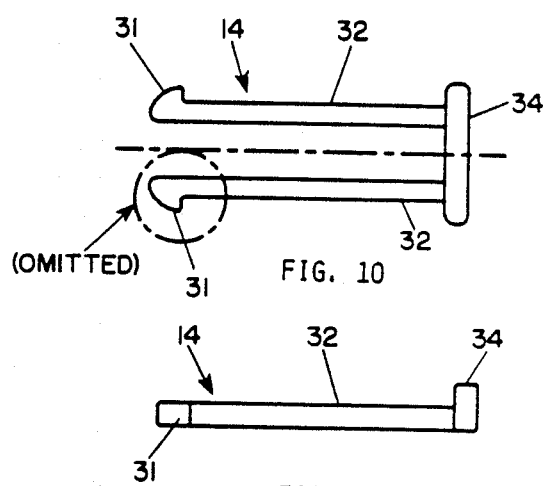
FIG. 10 is an elevational view of the proximal aspect of a retaining clip for permanently attaching the plastic insert to the base member.

The drawings are photo-reproductions of computer-generated mechanical drawings, and it has not been convenient to delete the phantom-line circles of FIGS. 4 and 10 representing details that are superfluous and omitted. Similarly, the parallel vertical lines in FIGS. 2 and 3 are unconventional according to strict drafting practice but will be understood to represent the lateral boundaries of the accurate surfaces.

DESCRIPTION OF THE PREFERRED EMBODIMENT

Figure 11:
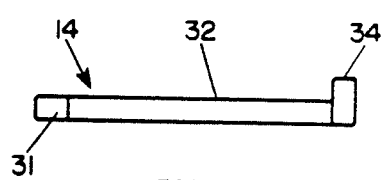
FIG. 11 is a plan view of the retaining clip depicted in FIG. 10.
Figure 12:
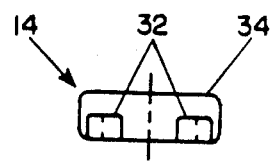
FIG. 12 is an elevational view of the medial aspect of the retaining clip.

The prosthesis according to the invention comprises four separate components—a unitary metatarsal component 11 (depicted in FIGS. 1 to 3) and a phalangeal component comprised of a base member 12 (depicted in FIGS. 4 to 6), a plastic insert 13 (depicted in FIGS. 7 to 9), and a retaining clip 14 (depicted in FIGS. 10 to 12).

Figure 1:
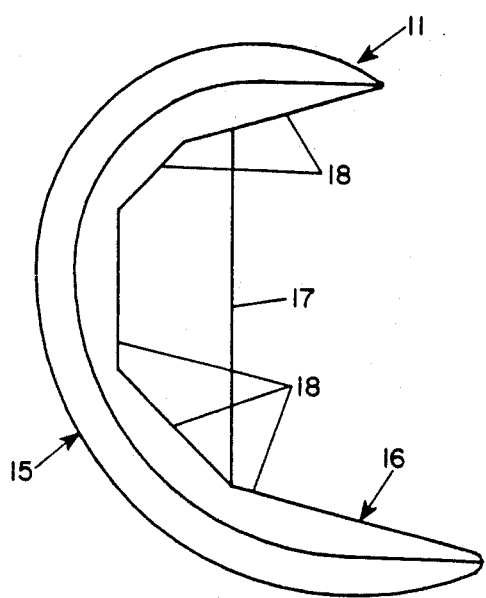
FIG. 1 is a side elevational view of the medial aspect of the metatarsal component of a right foot prosthesis according to the invention.
Figure 2:
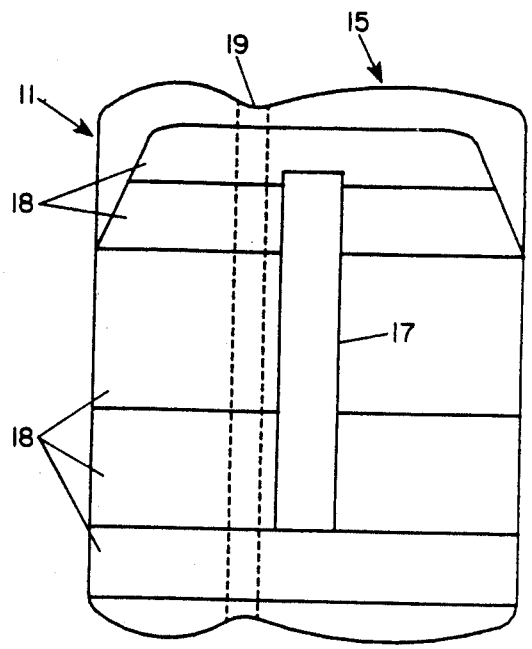
FIG. 2 is an elevational view of the proximal aspect of the metatarsal component depicted in FIG. 1.
Figure 3:
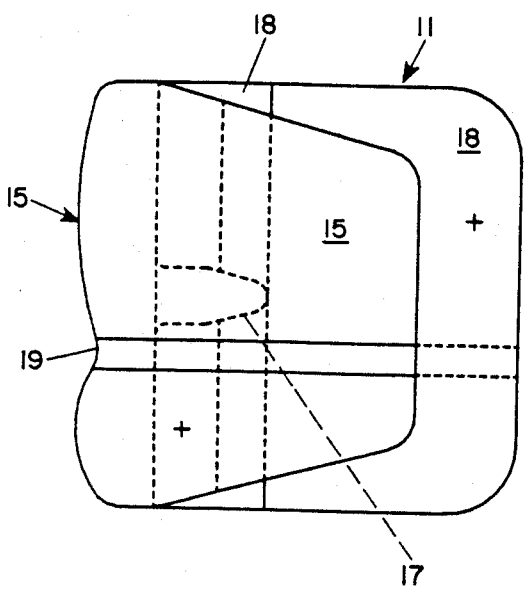
FIG. 3 is a plan view of the dorsal aspect of the metatarsal component.

Looking first to FIGS. 1 to 3, the metatarsal component 11 is designed for attachment by conventional commercially available bone cement to the resected end of the first metatarsal bone. The metatarsal component is preferably of one-piece cast metal construction. Known corrosion-resistant metal alloys such as Cobalt-Chromium-Molybdenum, ASTM F-75, are preferred for this application. The metatarsal component has a convex articular surface 15 designed to closely approximate the natural articular surface of the first metatarsal head, which it replaces. The proximal aspect 16 of this component is concave and has a web 17 and angled surfaces 18 which are designed to align with and be cemented to correspondingly shaped metatarsal osteotomies which the surgeon will have cut in the receiving end of the first metatarsal bone. It is desirable to provide grooves, such as diagonal crossing grooves (not shown) on the angled surfaces 18 at the plantar and dorsal extremities of the metatarsal component to enhance the attachment of the component to the cement. The web 17 extends perpendicularly to and forms a bridge between the surfaces 18 of the concave proximal aspect 16.

In this regard, the receiving portion of the metatarsal bone receives three resections—a dorsal cut, a plantar cut, and a distal cut, plus two chamfers. The dorsal cut is necessary to render the prosthesis capable of passive dorsi flexion ROM while minimizing the amount of bone resection. The dorsal and plantar cuts are each at a 15° angle to the bone axis to provide a taper lock fit of the prosthesis on the resected bone. This taper lock stabilizes the prosthesis and evenly distributes the load to the underlying cement and bone, preventing undesirable stress concentration and a more anatomic distribution of stress. The two chamfers bridge the dorsal/distal cut and plantar/distal cut junctions. These chamfers prevent thin cross-sections of bone at the junctions of the distal cut with the dorsal and plantar cuts, thus minimizing stress concentration at sharp corners.

It is believed that long stems inserted in metatarsal bones may increase the risk of long-term post-operative loosening and should be avoided if possible. The long moment arm of a stem, transferring high repetitive bending moments to the bone-cement and/or cement-prosthesis mantle near the end of the stem, may lead to cement fatigue and cracking or bone necrosis and loosening after several years. Since the metatarsal component is securely fixed in the dorsal and plantar directions, and because the taper lock provides stability in these directions as compressive loads increase, a long intramedullary stem, such as on the prior art metatarsal components, is not necessary. Instead, the metatarsal component has the wide web 17 for retention and to resist M-L shear forces.

The metatarsal component is produced in left foot and right foot versions, the purpose here being to approximate as closely as possible the natural shape of the articulating surface of the first metatarsal head. The remaining elements, i.e., the parts assembled to produce the phalangeal component, are adaptable for either right or left foot use merely by rotating the base member 12 180° about its proximal-distal axis.

As depicted in FIGS. 1 to 3, the metatarsal component 11 is intended for right foot use, the articular groove 19 being offset to the medial side of the foot as naturally occurs to accommodate the articular phalangeal ridge. It will be understood that a left foot version of the metatarsal component can be depicted by a mirror image of FIGS. 2 and 3.

The base member 12 of the phalangeal component (depicted in FIGS. 4 to 6) is preferably also of onepiece cast metal construction, e.g. Cobalt-Chromium-Molybdenum, ASTM F-75. The base member 12 has a stem portion 20 on the distal aspect 21 to facilitate positioning, stabilization and fixation of the member on the proximal phalanx with bone cement.

On the proximal surface 22 of the base member, there is a groove 23 precisely shaped so as to receive the plastic insert 13, described in more detail below. The groove 23 is open only on one end 24 for the receipt of the plastic insert. An overhanging flange 25 around the closed periphery of the groove prevents the plastic insert from lifting out of the groove.

Within the groove 23 is a deeper recess 26 shaped to receive and permanently retain a retention clip 14, also described in detail below.

In the preferred embodiment, the stem portion 20 is substantially rectangular in cross-section so as to resist rotational and shear forces. The stem 20 also preferably has longitudinal cement pockets 27 for added resistance to such forces.

The plastic insert 13 (depicted in FIGS. 7 to 9) provides the phalangeal surface 28 which articulates with the surface 15 of metatarsal component 11. Insert 13 is made of a high molecular weight plastic such as polyethylene (UHMWPE), thereby providing articulating surfaces having a metal-plastic interface between the metatarsal component 11 and insert 13. The articulating surface 28 of insert 13 is concave and shaped so as to smoothly slide against surface 15. A ridge 29 is designed to be in clearance with the articular groove 19 on the articulating surface 15 but to engage and restrict lateral medial translations and axial rotation. As noted above, this ridge is offset to the medial side of the foot so as to approximate the configuration of the anatomical joint.

Insert 13 is provided with an indentation or groove 30 shaped and sized to be received in and retained by the groove 23 and the rib 25 of the base member 12.

Once the insert 13 is slid into the groove 23, a retaining clip 14 (depicted in FIGS. 10 to 12) is inserted into the groove 26. The arms 32 on the retaining clip are resiliently bent inwardly toward each other as the clip is inserted into the groove 26 because projections 31 extend beyond the width of the groove. When these projections 31 encounter recesses 33 in the groove 26, they snap outwardly to permanently engage the recesses and thereby prevent the clip from being withdrawn. The extended end portion 34 of the clip then abuts the insert 13 and prevents the insert from being withdrawn from the open end 24 of the groove 23, with the result that the base member 12 and insert 13 are permanently attached.

While there exist other means of permanently attaching the base member to the insert, the means disclosed is preferred in that it permits the surgeon to quickly and easily perform this function once the appropriately sized insert is selected.

The retaining clip is preferably of titanium alloy, e.g. Ti-6A1-4V, ASTM F-67. Since the clip will be in contact with metal base member 12, it is important to note the preferred metal compositions thereof, Cobalt-Chromium-Molybdenum, ASTM F-75, and Ti-6A1-4V, ASTM F-67, respectively, are known to be resistant to galvanic corrosion in the presence of one another.

The assembly of the phalangeal metal base member and selected plastic insert with the retaining clip preferably is completed prior to implantation. The locking clip is positioned to encounter and withstand M-L shear forces rather than dorsal-plantar shear forces since the former are substantially lower than the latter forces during everyday usage of the foot.

An important feature of the present invention is the ease by which proper soft tissue tension may be obtained. Toward this end, the plastic insert 13 is made available in different thicknesses. Before the phalangeal component is inserted, the surgeon utilizes spacer blocks to determine the correct plastic insert thickness necessary for the desired soft tissue tension. In the preferred embodiment, the appropriate spacer block size represents the total thickness of both the mated metal base member with plastic insert and the thickness of the metatarsal component when implanted; i.e. the thickness approximates the proper (for tensioning) space between the resected end of the phalanx bone and the implanted metatarsal component. Since neither the height dimension of the metal base member 12 nor the thickness of the metatarsal component changes, the sizes (thicknesses) of the plastic inserts 13 may be labelled to correspond to the respective spacer block thicknesses to avoid confusion. The assigned sizes of the plastic inserts may not, therefore, represent actual polyethylene component thicknesses. If placement of the spacer blocks indicates that a size 12 mm spacer block achieves the desired soft tissue tension, a "12 mm" plastic component is selected for implantation, even though the plastic component actually will be less than 12 mm in thickness.

The variable plastic component thickness size feature also greatly reduces the number of products the hospital has to inventory to provide precision adjustment of soft tissue tension.

Thus according to the present invention there is provided a prosthesis which may be implanted and properly tensioned with relative ease. Once implanted, this prosthesis provides improved range of movement as well as improved strength and stability both of the resected bones and the prosthesis itself.

We claim:

1. A prosthesis for replacement of the first metatarsalphalangeal articulation comprising a metatarsal component and a phalangeal component, the metatarsal component having a convex articulating surface and concave distal aspect, the metatarsal articulating surface being curved so as to approximate the natural articular surface of the first metatarsal bone and furthermore to articulate smoothly with a phalangeal articulating surface of the phalangeal component, the phalangeal component including a metal base member and an insert of a high molecular weight plastic, the base member having a distal aspect adapted to engage and be secured to a resected end of the phalanx bone and a proximal aspect adapted to receive and have permanently attached thereto the insert, the insert having a proximal aspect that includes the phalangeal articulating surface, and the insert having a distal-proximal thickness selected so as to cause tension in the natural soft tissue surrounding the prosthesis after implantation which proximates the tension of the soft tissue of the natural metatarsalphalangeal articulation.

2. A prosthesis according to claim 1 wherein the base member has a groove on its proximal aspect adapted to receive the insert, and wherein the phalangeal component further includes means for permanently securing the insert in the groove.

3. A prosthesis according to claim 2 wherein the means for securing the insert in the groove comprises a second groove within the groove, the second groove being adapted to receive a retaining clip which, when inserted into the second groove resiliently engages a portion of the second groove to permanently retain the insert in the groove.

4. A prosthesis according to claim 3 wherein the retaining clip has two arms extending from an end portion, said arms having projections that engage recesses in the second groove, the end portion extending perpendicularly to and above the arms so as to abut the insert and permanently retain the insert in the groove when the projections are engaged in the recesses.

5. A prosthesis according to claim 1 wherein the distal aspect of the metatarsal component includes a web extending perpendicularly to and bridging the center of the concave distal aspect.

6. A prosthesis according to claim 5 wherein the distal aspect of the metatarsal component includes substantially planar angled surfaces so as to resist rotation of the component about the horizontal axis of the distal aspect.

7. A prosthesis according to claim 1 wherein the articulating surface of the metatarsal component has an articular groove and the articulating surface of the insert has an articular ridge, the articular groove and articular ridge being adapted to be in clearance with one another but being engageable to restrict lateralmedial translations and axial rotation.

8. A prosthesis according to claim 7 wherein the articular groove and articular ridge are so positioned that, when implanted in the patient, they are offset to the medial side of the foot.

* * * * *